United States Patent [19]

Vogt et al.

[11] Patent Number: 5,084,394
[45] Date of Patent: Jan. 28, 1992

[54] METHOD FOR CORRECTIVE CALIBRATION OF A FLOW CYTOMETRY USING A MIXTURE OF FLUORESCENT MICROBEADS AND CELLS

[76] Inventors: Robert F. Vogt, Bldg. 17, Room 2113, F-19, Centers for Disease Control, Atlanta, Ga. 30333; Abraham Schwartz, P.O. Box 4344, Hato Rey, P.R. 00919

[21] Appl. No.: 516,056

[22] Filed: Apr. 17, 1990

Related U.S. Application Data

[63] Continuation-in-part of Ser. No. 374,435, Jun. 30, 1989, which is a continuation-in-part of Ser. No. 128,786, Dec. 4, 1987, Pat. No. 4,857,451, which is a continuation-in-part of Ser. No. 805,654, Dec. 11, 1985, Pat. No. 4,774,189, which is a continuation-in-part of Ser. No. 685,464, Dec. 24, 1984, Pat. No. 4,767,206.

[51] Int. Cl.$^5$ .................. G01N 31/00; G01N 33/48; G01J 1/02
[52] U.S. Cl. .......................... 436/8; 436/10; 435/967; 356/42; 356/243
[58] Field of Search .............. 436/8, 10, 15, 19; 356/42, 243; 435/967

[56] References Cited

U.S. PATENT DOCUMENTS

| | | | |
|---|---|---|---|
| 4,035,316 | 7/1977 | Yen | 260/2.5 |
| 4,157,323 | 6/1979 | Yen | 260/29.7 |
| 4,247,434 | 1/1981 | Vanderhoff | 260/29.6 |
| 4,254,096 | 3/1981 | Monthony | 424/8 |
| 4,438,239 | 3/1984 | Rembaum | 525/54.1 |
| 4,511,662 | 4/1985 | Baran | 436/513 |
| 4,552,633 | 11/1985 | Kuma Kura | 204/159 |
| 4,605,630 | 8/1986 | Kung | 436/511 |
| 4,609,689 | 9/1986 | Schwartz | 523/202 |
| 4,656,144 | 4/1987 | Hosaka | 436/534 |
| 4,665,020 | 5/1987 | Saunders | 405/7 |
| 4,694,035 | 9/1987 | Kasai | 524/458 |
| 4,698,262 | 10/1987 | Schwartz | 428/402 |
| 4,699,826 | 10/1987 | Schwartz | 428/402 |
| 4,699,828 | 10/1987 | Schwartz | 428/402 |
| 4,714,682 | 12/1987 | Schwartz | 436/10 |
| 4,751,188 | 6/1988 | Valet | 436/63 |
| 4,774,189 | 9/1988 | Schwartz | 436/10 |
| 4,828,984 | 5/1989 | Schwartz | 435/7 |
| 4,868,126 | 9/1989 | Schwartz | 436/10 |

OTHER PUBLICATIONS

Brown et al., Ann. New York Acad. Sci., 468, pp. 93-103 (1986).
Vogt et al., Cytometry, 10, pp. 294-302 (1989).

*Primary Examiner*—David L. Lacey
*Assistant Examiner*—William K. Y. Chan
*Attorney, Agent, or Firm*—Olive & Olive

[57] ABSTRACT

The use of a combination of calibrated microbead populations with one or more calibrated biological cell populations to correct calibration of a flow cytometer for size and fluorescence intensity determinations of biological cell samples. The use of calibrated biological cells permits correction for factors related to the instrument and calibration microbeads so long as the excitation and emission spectra of the calibration microbeads, the calibration cells and the cell samples are all the same, respectively.

8 Claims, 5 Drawing Sheets

METHOD FOR CORRECTIVE CALIBRATION OF A FLOW CYTOMETRY USING A MIXTURE OF FLUORESCENT MICROBEADS AND CELLS

CROSS-REFERENCE TO RELATED APPLICATIONS

This application is a continuation-in-part of U.S. application Ser. No. 07/374,435 filed June 30, 1989; which is a continuation-in-part of U.S. application Ser. No. 07/128,786 filed Dec. 4, 1987, issued Aug. 15, 1989 as U.S. Pat. No. 4,857,451; which is a continuation-in-part of U.S. application Ser. No. 06/805,654 filed Dec. 11, 1985, issued Sept. 27, 1988 as U.S. Pat. No. 4,774,189, which in turn is a continuation-in-part of U.S. application Ser. No. 06/685,464 filed Dec. 24, 1984, issued Aug. 30, 1988 as U.S. Pat. No. 4,767,206. All parent patents and co-pending applications are hereby incorporated by reference.

BACKGROUND OF THE INVENTION

1. Field of the Invention

This invention relates to the combined use of calibrated fluorescent biological cells with calibrated fluorescent microbeads to compensate for different responses of different flow cytometers.

2. Description of the Related Art

Flow cytometers are used to analyze biological cells and particles in a fluid sample by intersecting a thin stream of the fluid by an illumination source, usually a laser beam. The resulting forward and right angle scattered and fluorescent light is analyzed with photomultiplier tubes (PMTs). The fluorescence channels of a flow cytometer, designated by F11, F12, F13, etc., are each set with barrier filters to detect a selected specific dye while filtering out signals from other wavelengths.

U.S. Pat. Nos. 4,714,682, 4,767,206, and 4,774,189, and U.K. Patent 2,172,104 describe calibration of a flow cytometer using highly uniform microbeads which have excitation and emission spectra that match that of the unknown samples, as well as describing the synthesis and composition of said highly uniform microbeads. Matching spectra of microbeads and cells in this way allows direct comparison of data among flow cytometers which have different barrier filters so long as the sample and the calibration microbeads are analyzed under the same instrument conditions and settings. The totality of these patents and all other patents and any other publications cited herein and/or referred to in the Cross-Reference to Related Applications is hereby incorporated herein by reference.

Fixed calf thymocyte nuclei stained with fluorescent dyes, e.g., fluorescein and phycoerythrin, were available in the public domain as samples between 1983 and 1987 under the trade name, Fluorotrol TM by Ortho Diagnostics Instrument Division (now part of Becton Dickinson Immunodiagnostic Systems). Fluorotrol TM thymocytes nuclei consisted of three different populations of fixed calf thymocytes nuclei: an unstained, a "dim" and a "bright" population. Fluorotrol TM was not designed as a calibration agent, but rather a reference material because the coefficient of variation on the fluorescence intensity of these cells was relatively wide, e.g., 10-20%, however they did possess similar size, refractive indices, and spectral properties as cellular samples normally analyzed with flow cytometers. References: Brown M, Hoffman R, Kirchanski S: Controls for flow cytometers in hematology and cellular immunology. Ann. NY. Acad. Sci. 468: 93-103, 1986; and Vogt, Cross, Phillips and Henderson (1989). A model System Evaluating Fluorescein-Labeled Microbeads as Internal Standards to Calibrate Fluorescence Intensity on Flow Cytometers. Cytometry 10: 294-302.

Similarly, when the size of cells is measured via forward light scatter with a flow cytometer which has been calibrated by relatively high refractive index calibration microbeads, the cells are found to be smaller than when measured by other means, e.g., light or scanning electron microscopy.

Although previously available microbeads have enabled instrument calibration, fluorescence intensity measurements of stained cells (e.g., lymphocytes stained with fluorochromes specific for CD4, a common lymphocyte surface marker) reveal that there is a large coefficient of variation (22.7%) when the cells are measured on different flow cytometers (see Example 4). A number of factors other than spectral matching appear to contribute to this imprecision, e.g., variation in excitation energy, geometry and material of the fluidics, and differences in the refractive index and scatter properties between the calibration microbeads and the cell samples.

One of the major sources of imprecision is due to the differences in the influence of excitation energy (i.e., laser power) on the fluorescence intensity (FI) of the calibration microbeads and the cell samples. As laser power increases, the FI of the microbeads becomes proportionally higher than the FI of the cell samples (see FIG. 8). This difference is probably related to the relatively low refractive index of cells (since a large component of their mass is water) and other factors which allows slightly more efficient excitation of the cells compared to the microbeads. This effect influences calibration of cell samples by causing a shift to lower MESF values (FIG. 9) (MESF units are measures of FI expressed as equivalent molecules of soluble fluorochrome that give the same FI as the cells or microbeads).

This difference may be seen from a comparison of FIGS. 1 and 2 which show illumination of microbeads with lower and higher laser beams, respectively, which is projected toward the bead from the left of the bead in the Figures. The smaller portion of bead illuminated with a low power laser beam results in a shift to lower numbers of MESF units in the channels.

These data suggested that some factors are required to account and correct for the differences and imprecision of fluorescence intensity and size measurements via flow cytometry.

It is therefore an object of this invention to provide cells and microbeads which are calibrated which may be used to adjust the calibration of flow cytometers by correcting the fluorescence intensity calibration plot of the flow cytometer.

It is a further object of this invention to provide a method of standardizing flow cytometers by correcting the fluorescence intensity calibration plot using calibrated cells and microbeads.

It is a further object of the invention to provide a method of increasing accuracy of size measurements using calibrated microbeads and calibrated cells.

Other objects and advantages will be more fully apparent from the following disclosure and appended claims.

SUMMARY OF THE INVENTION

The invention comprises the composition, and method of use of the combination of highly uniform calibrated microbeads and calibrated stained biological cells to calibrate the size and fluorescence intensity response of a flow cytometer to stained biological cells. The calibrated microbeads and calibrated stained cells may be used in mixtures or separately.

Preferably, the calibrated fluorescent microbeads and calibrated stained cells are mixed and analyzed simultaneously such that factors, other than spectral properties, which are related to differences in the material of the calibration microbeads may be adjusted for in the size and fluorescence intensity calibration plots of the flow cytometer. Since the right angle light scatter properties of the microbeads and cells differ considerably due to differences in refractive index, the microbeads and cells can be gated and analyzed separately providing the necessary correction factors (see FIG. 5). The correction factors are obtained by finding where the calibrated cells fall on the size and/or fluorescence intensity calibration plots of the microbeads and shifting those calibration plots respectively such that the calibrated cells read correctly on the shifted calibration plot. The difference between the original position of the calibration plot and the position it was shifted to is the required correction factor.

Other aspects and features of the invention will be more fully apparent from the following disclosure and appended claims.

DETAILED DESCRIPTION OF THE INVENTION AND PREFERRED EMBODIMENTS THEREOF

Figure 1:
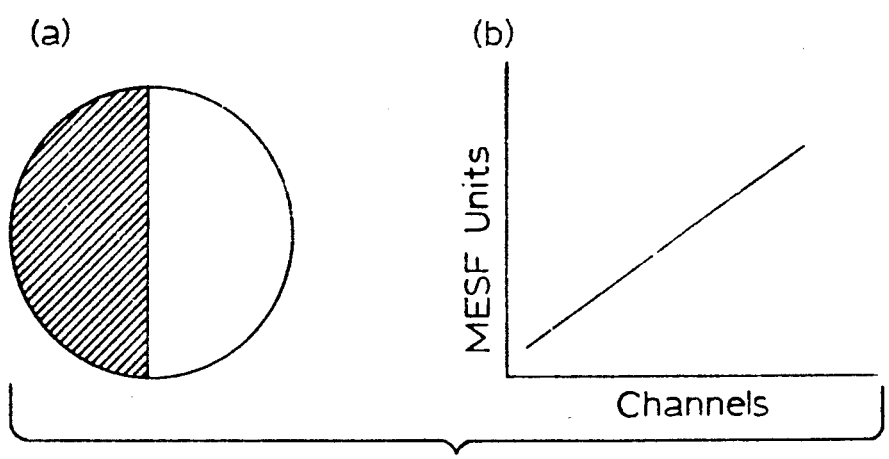
FIG. 1 shows illumination of microbeads (a) and calibration plot position (b) with a low power laser beam. The shaded area represents the proportion of fluorochrome molecules on the surface of the microbead that have emitted fluorescent light at this relatively low laser power.
Figure 2:
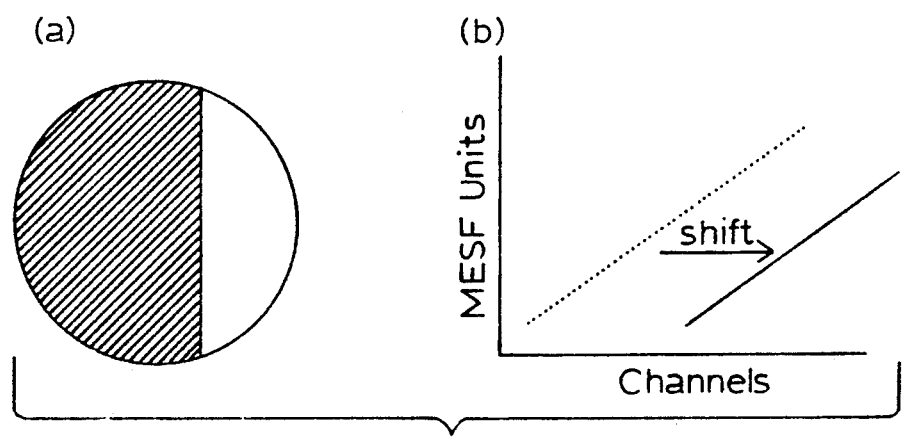
FIG. 2 shows illumination of microbeads (a) and calibration plot position (b) with a high power laser beam. The larger shaded area represents the increased proportion of fluorochrome molecules on the surface of the microbead that have emitted fluorescent light at this higher laser power.

The present invention includes a composition of highly uniform calibrated microbead populations and at least one calibrated cell population. The highly uniform calibration microbeads have excitation and emission spectra matching those of cell samples to be analyzed, and the calibrated cells comprise one or more populations of cells which are unstained, or stained with the same fluorochrome and exhibit the same excitation and emission spectra as the calibrated microbeads and cell samples to be analyzed.

The microbeads of the invention for use in adjusting calibration of a flow cytometer may be prepared as follows and as described in more detail in the above-cited patents:

(a) preswelling small microbeads (seeds);
(b) swelling the seed with a solution of monomers with convertible functional groups, e.g., epoxy groups on glycidyl methacrylate, and initiator;
(c) polymerizing the swollen seeds to produce highly uniform microbeads with convertible functional groups, e.g. epoxy groups;
(d) converting the surface functional groups, for example, to primary amines via reaction with diaminopropane;
(e) fluorescenating the microbeads with reactive fluorochromes, e.g., fluorescein isothiocyanate (FITC), to yield microbeads with the same excitation and emission spectra as the calibration cells and samples labeled with FITC, respectively; and
(f) calibrating the microbeads according to previously described methods (U.S. Pat. Nos. 4,714,682; 4,767,206; 4,774,189; and U.K. Patent 2,172,104).

Phycoerythrin, Texas red, allophycocyanin or other fluorescent dyes known in the art may be used with the appropriate modifications in the remaining steps of the preparation procedure as discussed in the patents cited herein.

The preferred calibrated cells are prepared as follows and described in more detail:

(a) gently mincing fresh calf thymus to form a slurry of tissue;
(b) suspending the slurry of tissue in a surfactant solution;
(c) filtering the tissue solution to form a single cell suspension;
(d) fixing the single cell suspension in an aldehyde solution;
(e) staining the fixed cells with a reactive dye, such as FITC or other fluorescent dye, to result in cells with an associated fluorescence;

(f) determining the fluorescence of the cells with a spectrofluorometer; and (g) determining the fluorescence intensity per cell in MESF units using the determination in step (f).

The preferred method of use of the calibrated microbeads and the calibrated cells in this invention for correcting a fluorescence intensity calibration plot of a flow cytometer is as follows:

(a) mixing microbeads from a plurality of calibrated microbead populations together with calibrated cells, said microbead populations and cells being calibrated for fluorescence intensity;

(b) analyzing the mixture on the flow cytometer;

(c) constructing an electronic gate region around the singlet population of the calibrated microbeads;

(d) obtaining histograms from the F11 channel;

(e) analyzing the histograms for peak (median) position;

(f) plotting the peak median position for each microbead population against calibrated fluorescence intensity values for that population;

(g) performing steps (c)–(f) for the calibrated cells;

(h) shifting the calibration plot line as defined by the microbeads to coincide with the values for the cells.

Methods for constructing an electronic gate, and other standard flow cytometry techniques are discussed in the FACScan ™ Research Software Users Guide, March 1988 (Becton Dickinson Immunocytometry Systems, Mt. View, Calif.) the disclosure of which is incorporated herein.

A "peak channel" is generally taken as the median channel, mean or modal channel in the series of channels comprising the peak when the parameter reading is plotted vs. the channel number.

Figure 3:
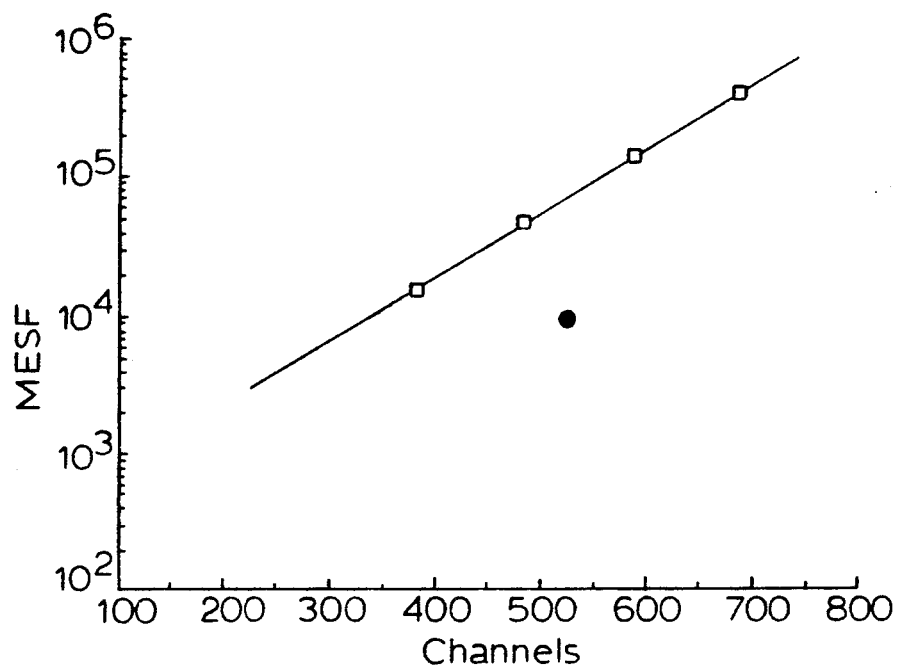
FIG. 3 is a calibration plot of fluorescence intensity constructed from fluorescence response of calibration microbeads (□), and the fluorescence response of a population of calibrated cells ( ), using the same instrument.
Figure 4:
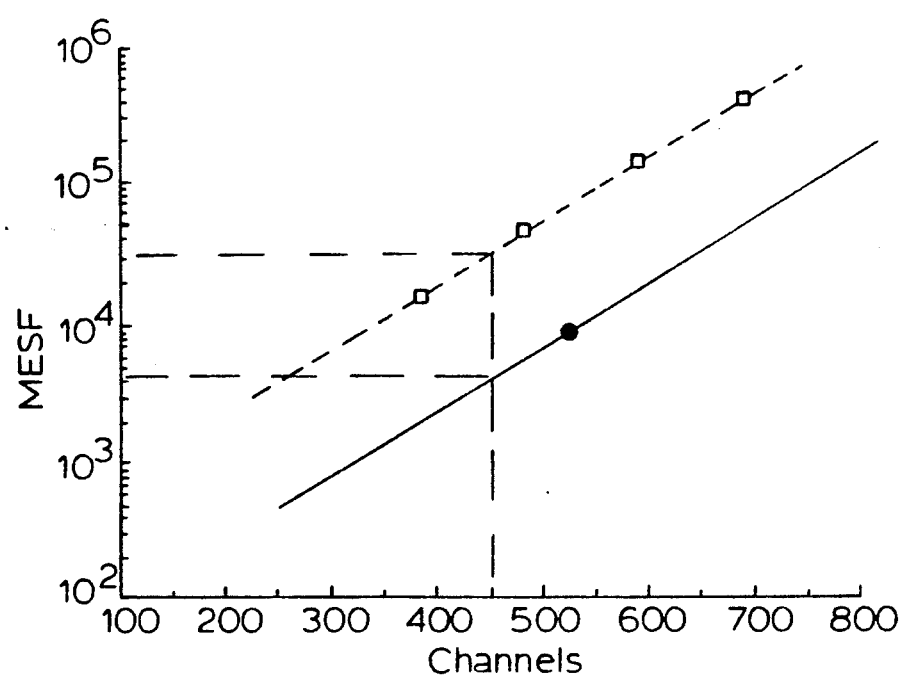
FIG. 4 is the calibration plot of FIG. 3 shifted such that the calibrated cell population falls on the correct position of the calibration plot.

FIGS. 3 and 4 show the unshifted calibration plot line (□) and cell value ( ). FIG. 4 shows the calibration plot line shifted (solid line) as in step (i) above. A dashed rectangular line shows the change in calibration amount according to the invention (from about $3.2 \times 10^4$ to $4.3 \times 10^3$ MESF). Values, such as fluorescence intensity or size, obtained for one or more unknown samples on a flow cytometer which has had its calibration plot corrected, may be accurately obtained through use of the shifted calibration plot line according to FIG. 4.

The present invention also includes highly uniform microbeads of different calibrated sizes but formed from the same material, and a calibrated cell population which has similar physical properties, for example, refractive index, as the cell samples to be analyzed.

The preferred method of use of these calibrated microbeads and cells in this invention for correcting a size calibration plot is as follows:

(a) mixing together calibrated cells and microbeads from a plurality of populations of calibrated microbeads, each of said populations consisting of microbeads of a highly uniform size, and the microbeads of each population differing in size from the microbeads of the other populations;

(b) analyzing the mixture on the flow cytometer;

(c) analyzing the forward scatter histogram for peak (median) positions of the microbeads and of the cells;

(d) plotting the peak (median) channels of the microbeads against the calibrated sizes of the microbeads;

(e) plotting the peak (median) channels of the cells against the calibrated sizes of the cells;

(f) shifting the calibration plot line as defined by the microbeads to coincide with the sizes for the cells.

The flow cytometer may be calibrated and corrected for whatever parameter the microbead and cell populations are calibrated for, and then a correct value of that parameter may be obtained for an unknown cell sample. Thus, for fluorescence intensity and size, respectively, as discussed above, the peak channels of the unknown sample(s) are determined on the corrected calibration line and the corresponding value for the selected parameter, e.g., fluorescence intensity or size in these examples, is read from the corrected (shifted) calibration plot.

Mixing the calibrated microbeads with the calibrated cell population for fluorescence intensity or size correction purposes is the preferred use of the invention; however, separate analysis of these components is also included within this invention.

When used with an unknown sample, the method of the invention for correction of calibration of a selected parameter comprises:

(a) providing a calibrated cell population and a plurality of microbead populations, each of said cell and microbead populations having a calibrated value for said parameter;

(b) determining the flow cytometer peak channel for each calibrated microbead population;

(c) determining the flow cytometer peak channel for the calibrated cell population;

(d) plotting the peak channels determined according to steps (b) and (c) as a function of the calibrated values of the population for which the peak value was determined;

(e) constructing a best fit calibration line through points plotted for the microbead population;

(f) shifting said best fit calibration line such that the plotted point for the cell population falls on the best fit line;

(g) determining the peak channel of unknown samples on the shifted calibration line; and (h) reading the corresponding values for said parameter from the corrected calibration line.

In the above methods, the flow cytometer calibration value (or parameter) being corrected may comprise fluorescence intensity or cell size.

The features and advantages of the present invention will be more clearly understood by reference to the following examples, which are not to be construed as limiting the invention.

EXAMPLES

Example 1

A set of highly uniform calibrated surface fluorescein labeled microbead populations, is prepared according to the methods of U.S. Pat. No. 4,714,682; 4,767,206; and 4,774,189; and UK Patent No. 2,172,104. The populations are all 5.8 u diameter and contain five sub-populations with different amounts of fluorescein: (1) 240,000 MESF; (2) 160,000 MESF; (3) 87,000 MESF; (4) 51,000 MESF; (5) 18,000 MESF.

A mixture of the five microbead populations is mixed with (a) FITC stained fixed calf thymocytes brightly labeled; (b) dimly labeled; and (c) unlabeled. The mixture of microbeads and cells are analyzed on a Coulter Epics 741 flow cytometer (Coulter Electronics, Hialeah, Fla.) by collecting 10,000 events in list mode files at different laser powers (50 mW to 1000 mW) for the 488 nm line. The setting of the FI PMT is readjusted at each laser power to give the same median channel value for the bright population. A sample containing CD4-stained human lymphocytes is also analyzed under the same conditions as the calibration mixture at each laser power.

Figure 5:
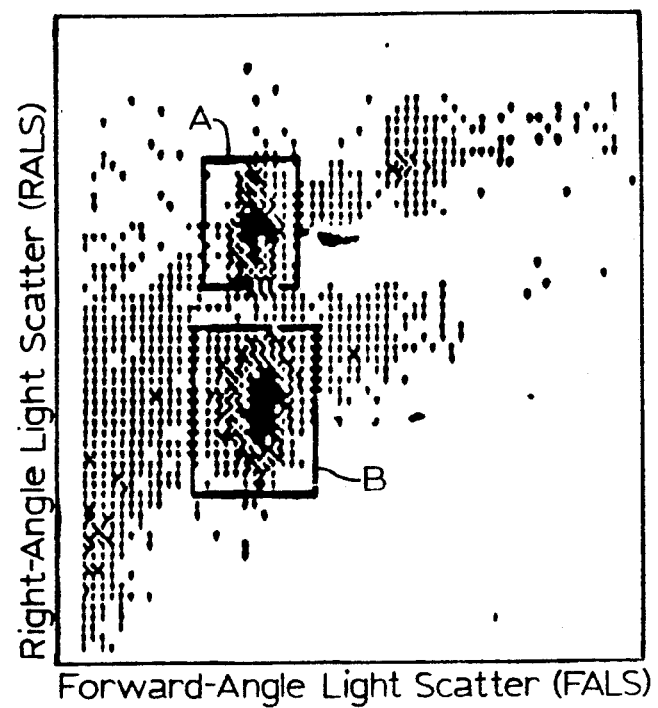
FIG. 5 is the forward vs right angle light scatter dot plot of calibrated microbeads and calibrated cells with a gate constructed around the singlet population of the microbeads (A) and with a gate constructed around the singlet population of the cells (B).
Figure 6:
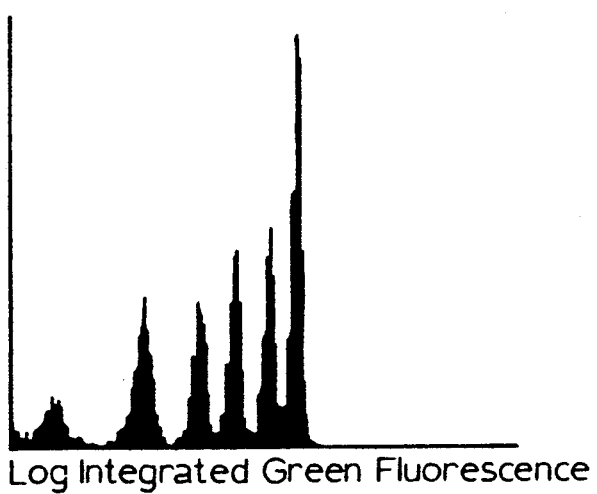
FIG. 6 is the F11 histogram of calibrated microbeads as gated in FIG. 5 (A).
Figure 7:
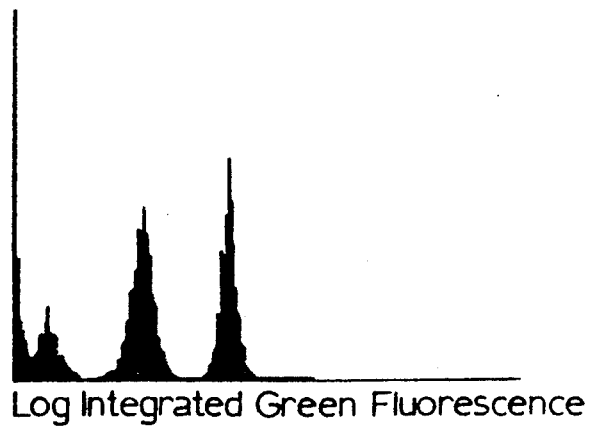
FIG. 7 is the F11 histogram of calibrated cells as gated in FIG. 5 (B).
Figure 8:
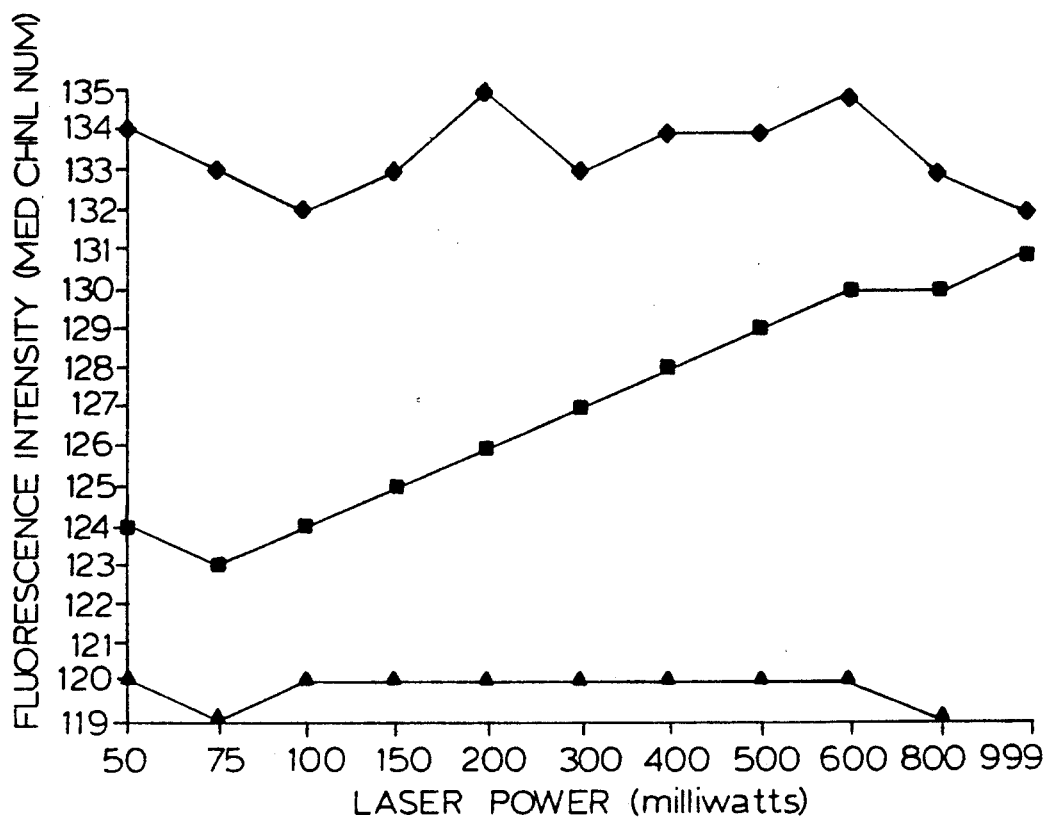
FIG. 8 is a graph of data showing that, as laser power increases, the FI of microbeads increases at a faster rate than the FI of Fluorotrol or CD4-labeled human lymphocytes. Microbeads are shown as ( ), fluorotrol is shown as ( ), and original lymphocytes are shown as ( ).
Figure 9:
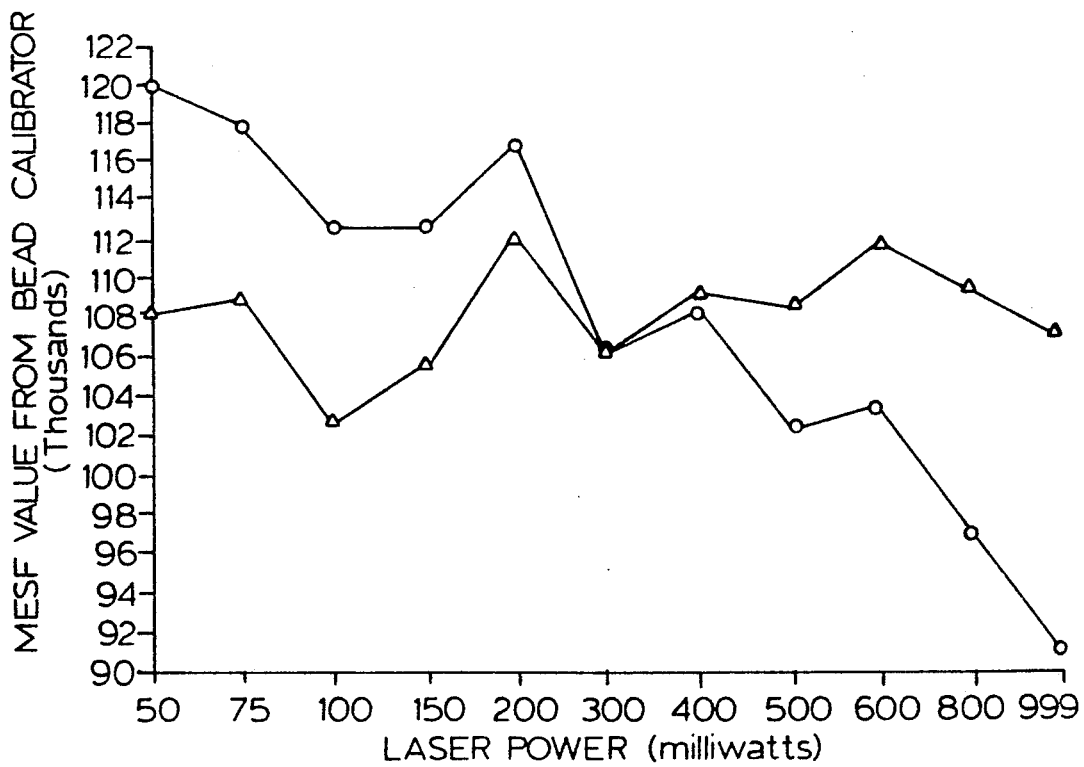
FIG. 9 is a graph of data showing that the effect of laser power on calibrating CD4-labeled human lymphocytes is to decrease the apparent FI as laser power increases. The figure also shows that this apparent decrease can be corrected by applying the correction process described herein. Original lymphocytes are shown as (○) and corrected lymphocytes are shown as (Δ)

Results are shown in FIGS. 8 and 9. FIG. 8 shows that, as the laser power is increased, the FI histogram channel values of the Fluorotrol and CD4-stained lymphocytes remain stable (because of the PMT adjustment), but the FI histogram channel value of the microbeads increases despite the adjustment. This shows that the FI of microbeads increases at a faster rate than the FI of cell samples as laser power becomes higher. FIG. 9 shows that the calibration and correction process described herein compensate for the decrease in FI values on CD4-stained lymphocytes as laser power increases. FIG. 5 shows the forward-angle vs log right angle light scatter dot plot shows the distinct population of microbead standards (A) and stained cells (B). FIG. 6 shows the log integrated green (fluorescein) fluorescence histogram from the microbead populations and FIG. 7 shows the histogram of the three thymocyte populations.

Example 2

A set of highly uniform calibrated surface fluorescein labeled microbead populations is prepared according to the methods of Example 1 and have diameters as follows: (1) 9.0 u; (2) 6.0 u; (3) 5.4 u; (4) 4.9 u; and (5) 4.4 u.

Example 3

The microbeads in Example 2 are mixed and run on a FACS Analyzer (Becton Dickinson & Co., Mountain View, Calif.) to calibrate the electronic volume channel of the instrument. A calibration curve is constructed using peak channels. A particular sample of lysed whole blood containing granulocytes and lymphocytes is analyzed in the instrument, resulting in a determination that the granulocytes are 10.3 u in diameter and the lymphocytes are 8.5 u in diameter. These measurements are verified by optical microscopy and scanning electron microscopy using critically point dried samples according to standard techniques. When the same microbeads are used to calibrate the forward light scatter channel of a FACScan flow cytometer (Becton Dickinson & Co.), the granulocytes and lymphocytes are found to be 12.1 and 10.4 u in diameter, respectively. When the calibration plot is shifted so that the plot coincided with the value for the granulocytes (10.3 u), the lymphocytes are found to fall in a channel coinciding to a diameter of 8.6 u, demonstrating than the shift is able to correct measurements for other cells.

Example 4

Figure 10:
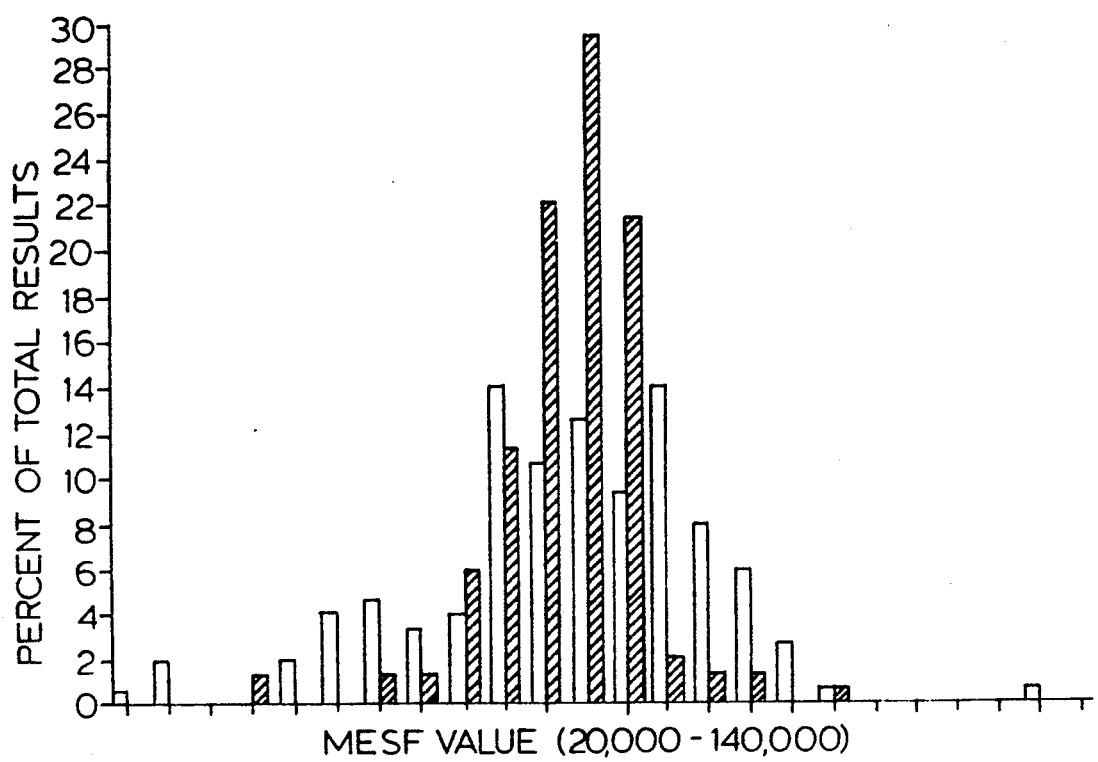
FIG. 10 is a graph of data showing that the imprecision of FI measurements between different instruments decreases significantly when the correction process described herein is applied. The corrected results are shown by the shaded bars and the uncorrected results are shown by the unshaded bars.

The fluorescence intensity of CD4 lymphocytes labeled with anti-mAb-FITC was determined with 45 different instruments in 38 different laboratories against a set of fluorescein surface-labeled calibrated microbeads similar to those in Example 1 (all were 5.8 u in diameter with fluorescence intensities of 240,000; 160,000; 87,000; 56,000; and 18,000 MESF, and blank). The fluorescence intensity values of the CD4 lymphocytes had an overall coefficient of variation (CV) (measure of imprecision) of 22.7% (FIG. 10). Each laboratory and instrument also analyzed the calibration mixture described herein. When the FI values of the CD4-stained lymphocytes were corrected by the process described herein, the distribution of results was much more precise and the CV decreased to 11.6%.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A method of correcting calibration of flow cytometers for a selected parameter for analysis of sample cells and decreasing a coefficient of variation between flow cytometer measurements of said parameter, said sample cells having excitation and emission spectra, said flow cytometers having channels, said method comprising:

(a) providing a calibrated cell population and a plurality of microbead populations, each of said cell and microbead populations having a calibrated value for said parameter, said cell population and said microbead populations exhibiting excitation and emission spectra which are the same as the excitation and emission spectra of the sample cells;

(b) determining a flow cytometer peak channel for each calibrated microbead population;

(c) determining a flow cytometer peak channel for the calibrated cell population;

(d) plotting the peak channels determined according to steps (b) and (c) as a function of the calibrated values of the population for which the peak value was determined;

(e) constructing a best fit calibration line through points plotted for the microbead population;

(f) correcting said best fit calibration line by shifting said best fit calibration line such that the plotted point for the cell population falls on the best fit calibration line and forms a shifted calibration line;

(g) determining the peak channel of unknown samples on the shifted calibration line; and (h) reading corresponding values for said parameter from the shifted calibration line.

2. A method of correcting calibration of flow cytometers according to claim 1, wherein the calibrated microbeads and calibrated cells are mixed together.

3. A method of correcting calibration of flow cytometers according to claim 1, wherein said selected parameter is size of the microbeads and cells, the value of said parameter is expressed in size units, and the size of the microbeads in each microbead population is different from the size of microbeads in other microbead populations.

4. A method of correcting calibration of flow cytometers according to claim 1, wherein each microbead population has a fluorescence intensity, the fluorescence intensity of each microbead population differs from the fluorescence intensity of the other microbead populations, and the fluorescence intensities of the microbead and cell populations are calibrated.

5. A method of correcting calibration of flow cytometers according to claim 1, wherein each microbead has a surface, said calibrated microbead populations have fluorescein bound to the surface of the microbeads, the calibrated cells are stained with fluorescein, and the microbeads and cells are calibrated in terms of equivalent molecules of soluble fluorochrome (MESF units)

6. A method of correcting calibration of flow cytometers according to claim 1, wherein each microbead has a surface, said calibrated microbead populations have phycoerythrin bound to the surface of the microbeads, the calibrated cells are stained with phycoerythrin, and the microbeads and cells are calibrated in terms of equivalent molecules of soluble flurochrome (MESF units).

7. A method for correcting a fluorescence intensity calibration plot for analysis of an unknown sample, said unknown sample having excitation and emission spectra, comprising:
(a) mixing microbeads from a plurality of calibrated microbead populations together with calibrated cells, said microbead populations and cells being calibrated for fluorescence intensity and having excitation and emission spectra which are the same as the excitation and emission spectra of the unknown sample;
(b) analyzing the mixture on a flow cytometer, wherein said flow cytometer has an F11 channel and wherein said analysis results in formation of a singlet population;
(c) constructing an electronic gate around the singlet population of the calibrated microbeads;
(d) obtaining histograms from the F11 channel;
(e) analyzing the histograms for peak position and determining a peak median position for each microbead population;
(f) plotting the peak median position for each microbead population against calibrated fluorescence intensity values for the population to form a calibration plot line;
(g) performing steps (e)–(f) for the calibrated cells;
(h) correcting said calibration plot line by shifting the calibration plot line as defined by the microbeads to coincide with the values for the cells to form a shifted calibration plot line;
(i) determining the peak channel of the unknown sample on the shifted calibration line; and
(j) reading fluorescence intensity values corresponding to the peak channel of the unknown sample from the shifted calibration plot line.

8. A method for correcting a size calibration plot for analysis of an unknown sample, said unknown sample having an excitation and emission spectra, comprising:
(a) mixing together calibrated cells and microbeads from a plurality of populations of calibrated microbeads, each of said populations consisting of microbeads of a highly uniform size, and the microbeads of each population differing in size from the microbeads of the other populations, said sizes of the microbeads and cells being calibrated, said calibrated cells and microbeads having excitation and emission spectra the same as the unknown sample;
(b) analyzing the mixture of cells and microbeads on a flow cytometer and obtaining a forward scatter histogram;
(c) analyzing the forward scatter histogram for peak positions of the microbeads and of the cells;
(d) plotting peak channels corresponding to the peak positions of the microbeads against calibrated sizes of the microbeads to form a calibration plot line;
(e) plotting peak channels corresponding to the peak positions of the cells against the calibrated sizes of the cells;
(f) correcting the calibration plot line by shifting the calibration plot line as defined by the microbeads to coincide with the sizes for the cells to form a shifted calibration plot line;
(g) determining a peak channel of the unknown sample on the shifted calibration plot line; and
(h) reading sizes corresponding to the peak channel of the unknown sample from the shifted calibration plot.

* * * * *